United States Patent [19]
Humphries, Jr. et al.

[11] Patent Number: 6,163,971
[45] Date of Patent: Dec. 26, 2000

[54] AUTOMATIC FOOT SIZING APPARATUS

[75] Inventors: Herbert Brooks Humphries, Jr.; Frank Rene Gruber, both of Monroe, N.C.

[73] Assignee: Accura Design, Inc., Monroe, N.C.

[21] Appl. No.: 09/150,772

[22] Filed: Sep. 10, 1998

Related U.S. Application Data

[60] Provisional application No. 60/058,437, Sep. 10, 1997.

[51] Int. Cl.[7] ..................................................... A61B 5/117
[52] U.S. Cl. ................................ 33/515; 33/511; 33/512; 33/3 R; 33/3 A; 33/3 B; 33/3 C
[58] Field of Search ............................. 33/511, 512, 515, 33/3 R, 3 A, 3 B, 3 C, 706, 707

[56] References Cited

U.S. PATENT DOCUMENTS

| | | | |
|---|---|---|---|
| 2,605,548 | 8/1952 | Clarke | 33/3 B |
| 2,657,463 | 11/1953 | Spencer | 33/3 A |
| 3,173,208 | 3/1965 | Dana | 33/3 R |
| 3,192,627 | 7/1965 | Levitt et al. | 33/515 |
| 3,328,882 | 7/1967 | Blivice | 33/3 C |
| 3,375,586 | 4/1968 | Kennedy | 33/3 R |
| 3,408,740 | 11/1968 | Saad et al. | 33/3 R |
| 3,457,647 | 7/1969 | Cohen et al. | 33/3 R |
| 3,931,680 | 1/1976 | Greensides | 33/3 B |
| 4,164,815 | 8/1979 | Solomon | 33/515 |
| 4,294,014 | 10/1981 | Baumann et al. | 33/3 B |
| 4,395,826 | 8/1983 | Bidegain et al. | 33/3 C |
| 4,538,353 | 9/1985 | Gardner | 33/515 |
| 4,604,807 | 8/1986 | Bock et al. | 33/3 C |
| 5,025,476 | 6/1991 | Gould et al. | 33/3 B |
| 5,128,880 | 7/1992 | White | 33/512 |
| 5,164,793 | 11/1992 | Wolfersberger et al. | 33/3 R |
| 5,691,923 | 11/1997 | Adler et al. | 33/707 |
| 5,729,905 | 3/1998 | Mathiasmeier et al. | 33/3 R |
| 5,793,201 | 8/1998 | Nelle et al. | 33/706 |
| 5,979,067 | 11/1999 | Waters | 33/512 |
| 6,029,358 | 2/2000 | Mathiasmeier et al. | 33/3 R |

*Primary Examiner*—Diego Gutierrez
*Assistant Examiner*—Yaritza Guadalupe
*Attorney, Agent, or Firm*—Kennedy Covington Lobdell & Hickman

[57] ABSTRACT

The present invention discloses an automatic foot-sizing apparatus having a base, at least one motor, an activation switch activated by the proximity of the ball of the person's foot, at least three panels driven by the motor for engaging the heel, the toe projecting forwardmost from the foot, and the outer edge of the person's foot being measured, a distance-determining means associated with each panel for producing data representing how far each panel travels from a known starting position until engaging the person's foot, and a microprocessor for detecting activation of the switch, for controlling the motor, for receiving the distance-representing data, and for converting the distance-representing data into a shoe size. The apparatus provides a visual display for providing measurement information to the user and a keypad entry to enable the user to start the apparatus and to indicate the age, sex, and arch-type of the person being measured. A user can also input whether the shoe size should be adjusted to account for variations between shoe manufacturers and whether the shoe size should be displayed in a foreign or domestic shoe size unit.

16 Claims, 14 Drawing Sheets

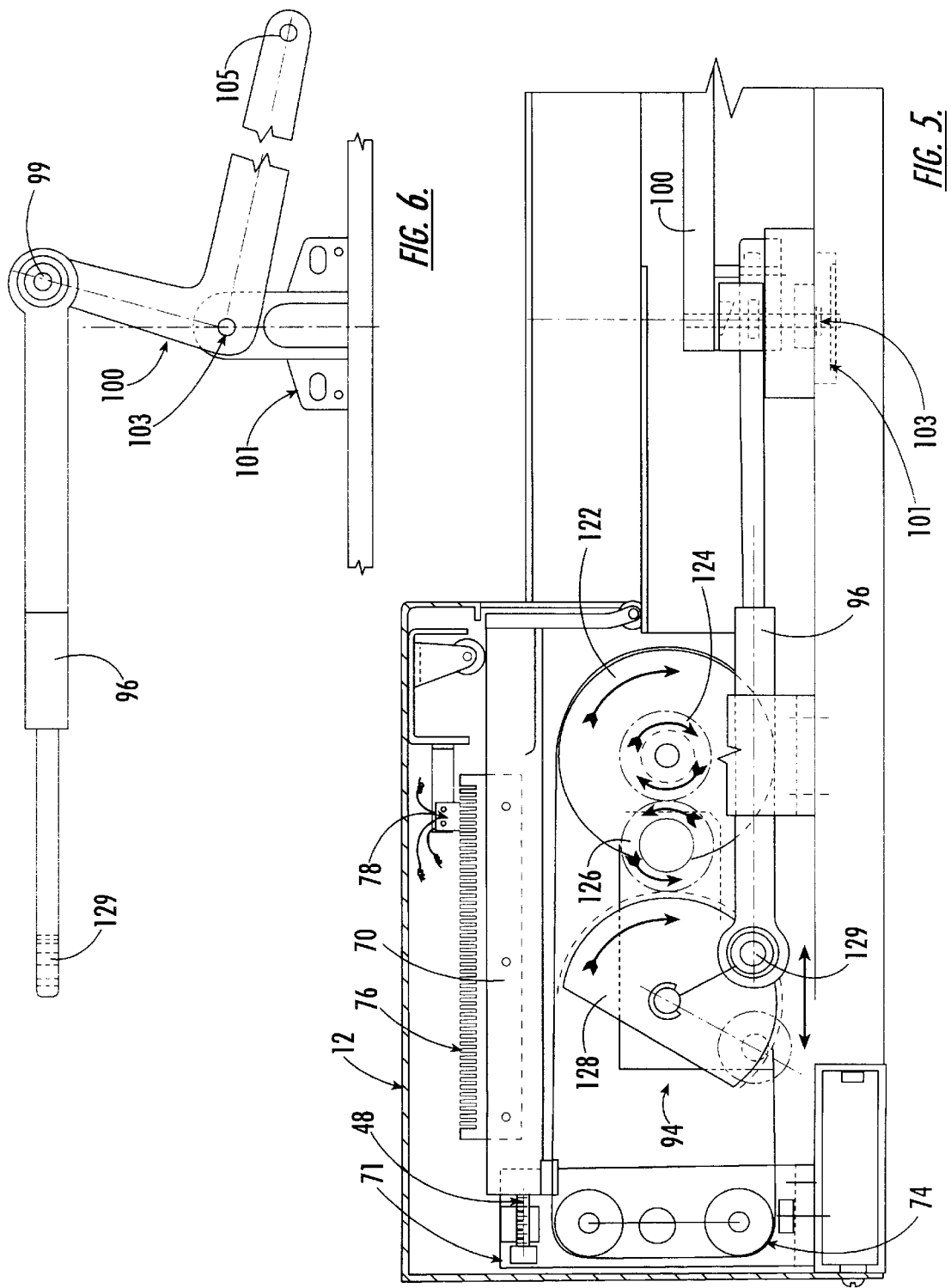

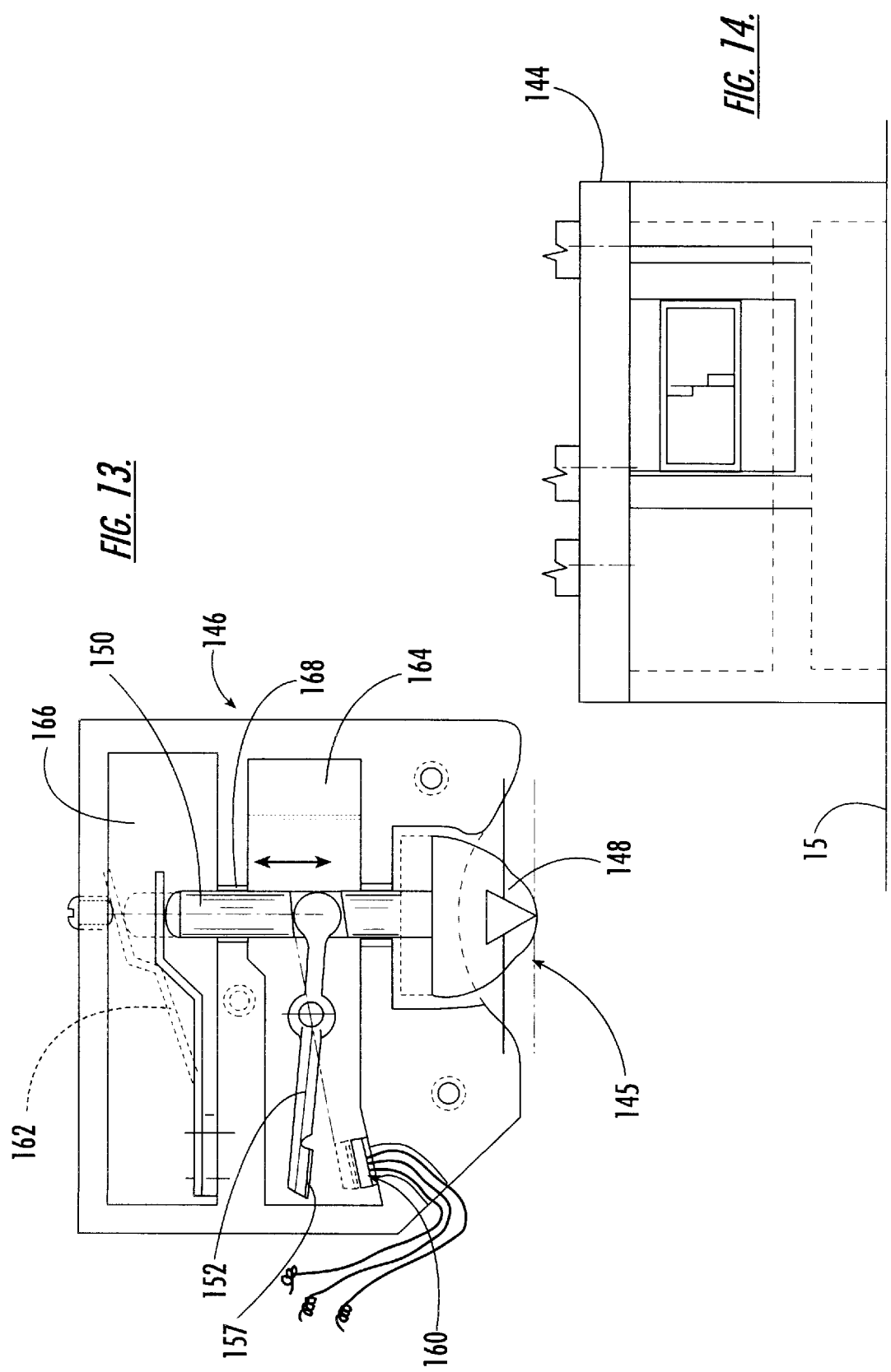

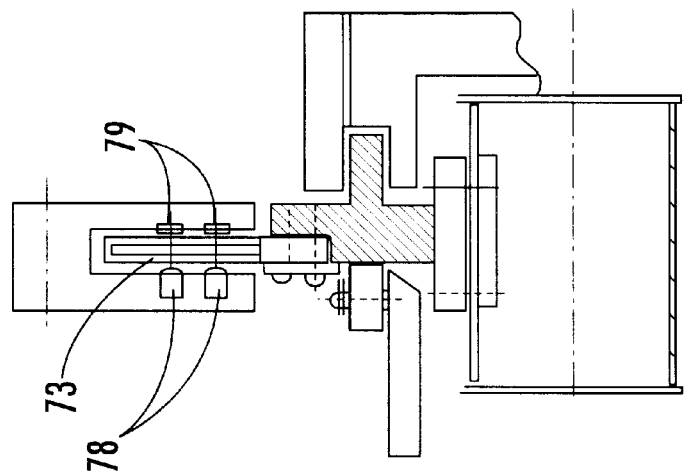
FIG. 19.
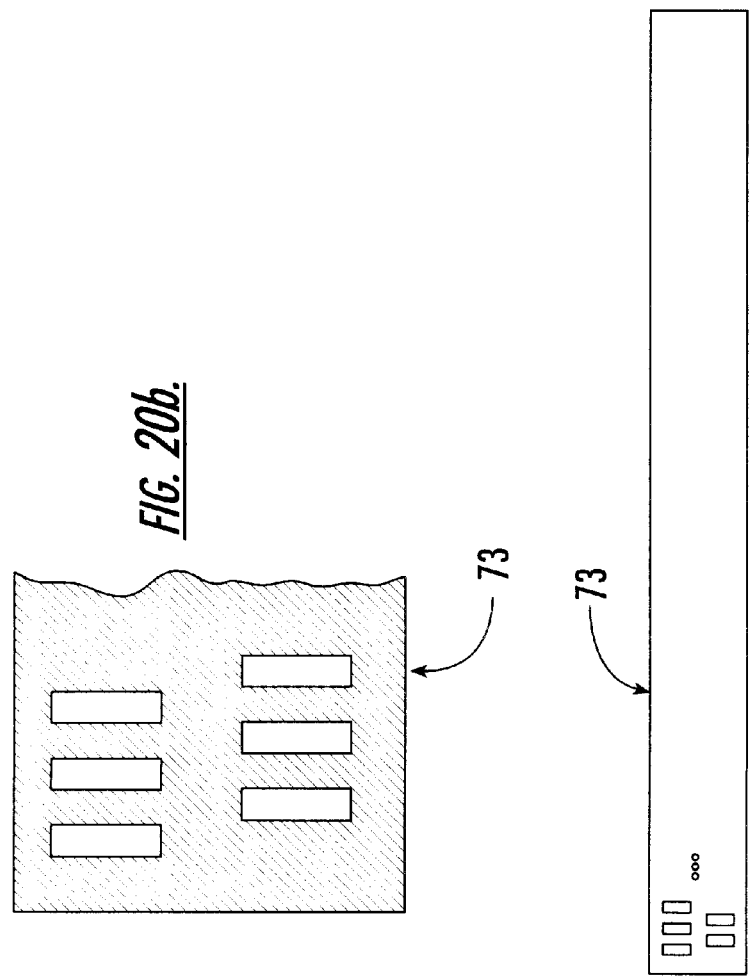
FIG. 20b.
FIG. 20a.

AUTOMATIC FOOT SIZING APPARATUS

CROSS-REFERENCE TO RELATED APPLICATION

This disclosure incorporates and has the priority of the U.S. Provisional Application Ser. No. 60/058437, filed Sep. 10, 1997, entitled AUTOMATIC FOOT SIZING APPARATUS.

BACKGROUND OF THE INVENTION

The present invention relates broadly to devices for determining the size of a person's foot and, more particularly, to a device for automatically measuring the dimensions of a person's foot and providing a displayed output indicating the preferable shoe size for each foot with the shoe size being tailored to a variety of different units (country-specific and shoe manufacturer-specific).

Proper shoe sizing is an important aspect of life. Improperly fitted shoes, whether because of improper length, width, instep, or some combination of all three, can lead to discomfort, pain, or annoyance. Many generations of shoe purchasers have relied upon a manual shoe sizing device wherein a scaled platform is provided with a heel locator, a locator for the ball of the foot and scale graduations to determine the size from the position of the heel, toe and ball of the foot. This device, which relies upon human placement of the foot and human determination of the measurement, is of questionable precision and accuracy.

In recent years, there have been attempts to provide for more accuracy and precision through the use of devices which automatically determine the size of a person's foot. For example, Wolfersberger et al., U.S. Pat. No. 5,164,793, discloses a device which uses an optical scanner to produce a three-dimensional image of the foot, which a computer then converts into a shoe size recommendation. White, U.S. Pat. No. 5,128,880, discloses a device that scans the bottom facing surfaces of a foot and electronically displays the scan of the foot on a visual display. Bock et al., U.S. Pat. No. 4,604,807, electronically measures the size of a person's foot using optics. The foot is placed into a well on the side of the apparatus and light is used to create a shadow of the foot on a mirror with the image being recovered by a camera for display.

All of these optical scanning devices are relatively complex, large, heavy, expensive, and require precise adjustment to maintain proper sizing.

BRIEF SUMMARY OF THE INVENTION

It is an object of present invention to provide an automatic foot-sizing device which is compact, light-weight, inexpensive, and easy to use.

It is a further object of the present invention to provide an automatic foot-sizing device of an electromechanical nature which is not only fast and accurate but also delicate and comfortable on the foot or feet being measured.

It is also an object of the present invention to provide an automatic foot-sizing device which can electronically store a large volume of measurement data for display or downloading to another computer.

It is another object of the present invention to provide an automatic foot-sizing device that can provide a recommended shoe size and at least one alternate shoe size in a variety of country-specific size units and for a variety of shoe manufacturers.

To that end, the present invention provides an electromechanical device for determining a shoe size corresponding to a person's foot size. The device is configured as a generally flat structure having a plurality of mechanical devices which, when activated, measure the various dimensions of a foot or feet placed on the flat structure. A microcomputer/controller converts the physical measurements into an actual shoe size recommendation for each foot, taking into account a number of variables, including country-specific shoe size units and known variations between shoe sizes from different shoe manufacturers. Such variables can be adjusted by the shoe customer or device operator, as desired.

Two main embodiments of the present invention are disclosed herein. The first embodiment allows a person to measure both of his feet simultaneously on a single device. The second embodiment, using a smaller device with essentially half of the mechanical components of the first embodiment, allows sizing of only one foot or of two feet in sequence. The basic mechanical and electrical principles disclosed hereinafter are essentially the same for both embodiments.

With either embodiment, the basic foot-measuring device includes a platform having a locator for the ball of the foot/feet disposed thereon. For the two-foot embodiment, the ball locator is mounted in approximately the center of the platform for engagement with the ball of both feet. For the one-foot embodiment, the ball locator is mounted on one side of the platform for engagement with the ball of one foot at a time. Once a person's foot/feet are properly placed against the ball locator, measurement panels slide horizontally along the foot platform until coming into contact with the person's foot/feet. The panels associated with each foot include a heel panel, a toe panel, and a side or width measurement panel. Each of the heel and toe panels have wheels mounted to their lower edges which allow for smooth movement. The wheels, which are disposed within grooves on the foot platform, also help guide the panels.

It is preferable that the panels be driven by a stepper motor. Although one stepper motor could be used through gears and links to drive all of the panels in either the one-foot or two-foot embodiment, it is preferable that two stepper motors be used with either embodiment. For the one-foot embodiment, one motor drives the toe panel while another motor drives the heel panel. The width panel is then mechanically inter-linked to be driven by either one of these two motors. For the two-foot embodiment, one motor drives both toe panels while another motor drives both heel panels. Also with the two-foot embodiment, one of the motors can be mechanically inter-linked to drive the width measurement panel for one foot while the other motor can be mechanically inter-linked to drive the width measurement panel for the other foot.

Each stepper motor is operatively connected to a drive shaft using a toothed belt. For the one-foot embodiment, the drive shaft is connected through a slip clutch to a rotating drum. For the two-foot embodiment, the drive shaft and a drive shaft extension are connected to a pair of rotating drums through separate slip clutches. The slip clutches will be discussed in greater detail hereinafter. A support belt, preferably a steel belt, is trained around each rotating drum and held in tension around a pair of adjustable rollers such that the support belt forms an elongate endless belt. Each toe and heel measuring panel is mounted to one end of an elongate bracket, which connects at its other end onto the top surface of the support belt. Since only the top surface of the support belt can be used to drive each elongate bracket and, correspondingly, each toe and heel panel, the top surface of the support belt must be long enough to enable the toe and heel panels to extend from an "at rest" position to a fully extended position. Mechanical stoppers prevent the steel belt from rotating too far in either direction.

Each width panel is driven by a gear system attached to one of the drive shafts or drive shaft extensions which converts the rotary motion of the drive shaft into a linear motion associated with a mechanical link. The mechanical link is connected to a bell crank and the bell crank acts to move the width measuring panel in a direction generally perpendicular to the movement of the heel and toe panels. All panel movement is coordinated by a microprocessor.

As previously stated, both embodiments of the present invention use a locator for the ball of the foot/feet disposed thereon. The ball locator serves several purposes: (1) properly locating a person's foot/feet on the device; (2) activating the device using a switch or switches which are triggered when the person's foot/feet are properly placed; and (3) optionally, indicating whether the person using the device is an adult or a child based upon which switches are activated. If the ball locator does not have the optional separate switches for an adult or a child, then such information would need to be input into the device microprocessor by the customer or device operator. Thus, for the two-foot embodiment, the device could have two activation switches (one for each foot) or four switches (two for each foot, one for adults and one for children). For the one-foot embodiment, the device could merely have one switch for all.

When a measurement is initiated, each of the panels extends from its "at rest" position until coming into contact with the foot disposed on the platform. Since each stepper motor drives more than one panel and since the various panels could contact the surface of a person's foot at different times, it is necessary for the stepper motors to run until all the panels have come into contact with the person's foot/feet. For this reason, the slip clutch associated with each panel can be advantageously used. Preferably, to provide a longer life and minimize the amount of maintenance and adjustments necessary to the device, the slip clutch should be magnetic or electromagnetic rather than frictional. In practice, each magnetic slip clutch must provide sufficient torque to drive a panel against the person's foot and maintain it against the foot until all three panels are at rest against the foot for a predetermined period of time, such as, for example, one second. In this manner, the magnetic slip clutch minimizes the amount of pressure exerted by each panel onto the foot so that not only is the foot not crushed between the various panels but the amount of pressure exerted on the foot is comfortable (i.e. low mass, at fast feed or low inertia, and steady torque). Once all three panels have come into contact with the foot, the device records the measurements of the foot/feet and immediately reverses the direction of the stepper motors so that the panels return to their "at rest" positions.

The present invention measures the size of a person's foot indirectly by measuring how far each panel moves from its "at rest" position until contacting the foot. More specifically, a microprocessor associated with the device, having been preprogrammed with the specific distances between the toe and heel panels in their "at rest" positions and between the ball locator and the width panel in its "at rest" position, can calculate the person's shoe size.

For example, a universal foot unit, which is the basis for all shoe sizes, is approximately one-third of an inch. Most shoes and most conventional foot-measuring systems merely resolve measurements to one-half a unit. By way of comparison, the present invention is highly accurate, measuring a customer's foot from between one-fourth to one-eighth of a universal foot unit, depending upon which of the following measuring embodiments is used.

In one embodiment, a comb-like structure is provided on an upper surface of the support bracket of each heel and toe panel and slider associated with the width panels. A light emitting diode (LED) is provided along with a photocell sensor adjacent the comb and in alignment therewith such that as the comb is caused to move linearly, the photocell senses a series of openings and blocking members. By counting the spaces, a fairly accurate determination (down to one-sixth of a universal shoe size interval) may be made as to the distance that the panel had to extend to contact the person's foot.

In another embodiment, an LED can be mounted across from a photosensitive transistor. A photo-etched glass plate having a series of evenly spaced slots is mounted to the support bracket of each panel and disposed between the LED and photosensitive transistor. As the panel and, thus, the glass plate move, the transistor counts the number of light pulses passing through the slots in the glass plate. This embodiment also provides a fairly accurate determination (down to one-fourth of a shoe size interval) of the distance the panel had to extend to contact the person's foot. For even more accurate measurements (down to one-eighth of a shoe size interval), two sets of LEDs and photosensitive transistors can be positioned across from each other. In this embodiment, the photo-etched glass plate can be manufactured to have two offset rows of alternating slots. One row of slots is disposed between one LED/transistor pair and the other row is disposed between the other LED/transistor pair. The slots and rows are offset so that, as the panel and glass plate move, light from the LEDs will alternate passing through one slot in one row at a time. This embodiment basically doubles the accuracy available with only one LED/transistor pair and one row of slots.

It should also be noted that, instead of using a linear comb or plate as described in either of the above two embodiments, a circular disk having notches or slots formed therein could alternatively be used to determine the distance each panel travels.

As is conventional, the present invention may be powered by household current or by a rechargeable battery. In addition, a battery backup power supply may be used to retain foot sizing data and information in computer memory during unexpected power interruptions. In the preferred embodiment, the base platform is made of a low-profile molded plastic. This not only makes it easier for a person to step onto the device to get his foot or feet measured but also minimizes the overall weight of the device. Optionally, steel rods or the like may be inserted along preformed slots within the underside of the molded base to provide reinforcement to the plastic and maintain rigidity of the base.

An operational interface provides a keypad and a display with an internal preprogrammed microprocessor computer. Before activating the measurement device, the operator or customer inputs information from the keyboard into the microprocessor, including a start command, a selection for male or female, a selection for adult or child (unless such an indication is made using the designated switch at the ball locator), and a selection for the user's instep type (e.g. average or high). After these entries have been made, the device is ready to measure the foot/feet of the customer. Once the foot/feet are properly placed on the platform and the switch/switches in the ball locator are depressed, the device activates and the panels engage and disengage from the customer's foot—all within a few seconds. This sizing measurement data is transferred to the computer, which compares this data with a table of shoe sizes. The computer then displays recommended shoe sizes and alternative shoe sizes, such as the next best fit departing from the optimum fit, including longer length with a narrower width or shorter length with a wider width. The unit also offsets its scale between male and female and children, depending upon the original entry by the customer or operator. If desired by the customer or device operator, the device can also be programmed to provide recommended and alternative shoe sizes that factor in known size variations between different shoe manufacturers. The measurements are recorded in the computer memory, which allows them to be retrieved and, if desired, transferred to an external computer. Being able to store and download such measurement data is useful for developing shoe and customer statistics, which, in turn, provides useful information for making retail purchasing and manufacturing decisions. The measurements may also be converted or interpreted in foreign or domestic shoe size units by making a selection on the keyboard. In the preferred embodiment of the present invention, shoe sizes may be displayed in country-specific units corresponding to the United States, Japan, Europe, or the United Kingdom.

By the above, the present invention provides an accurate, rapid foot measurement, in a system that is light-weight, compact, inexpensive to manufacture, and easy to maintain. The present invention also allows for storage and subsequent retrieval of the measuring data obtained by the measurement device.

BRIEF DESCRIPTION OF THE DRAWINGS

FIG. 5 is a side view of a portion of the mechanism driving width measuring devices;

FIG. 6 is a top view of a portion of the mechanism driving width measuring devices;

FIG. 13 is a top view of another embodiment of the ball locating system;

FIG. 14 is a side view of the ball locating system illustrated in FIG. 13;

FIG. 19 is a side diagrammatic view of another embodiment for measuring the distance traveled by measurement panels;

FIG. 20a is a side view of a glass-etched plate used in conjunction with the measuring system illustrated in FIG. 19; and FIG. 20b is an enlarged side view of the glass-etched plate illustrated in FIG. 20a.

DESCRIPTION OF THE PREFERRED EMBODIMENT

Figure 1:
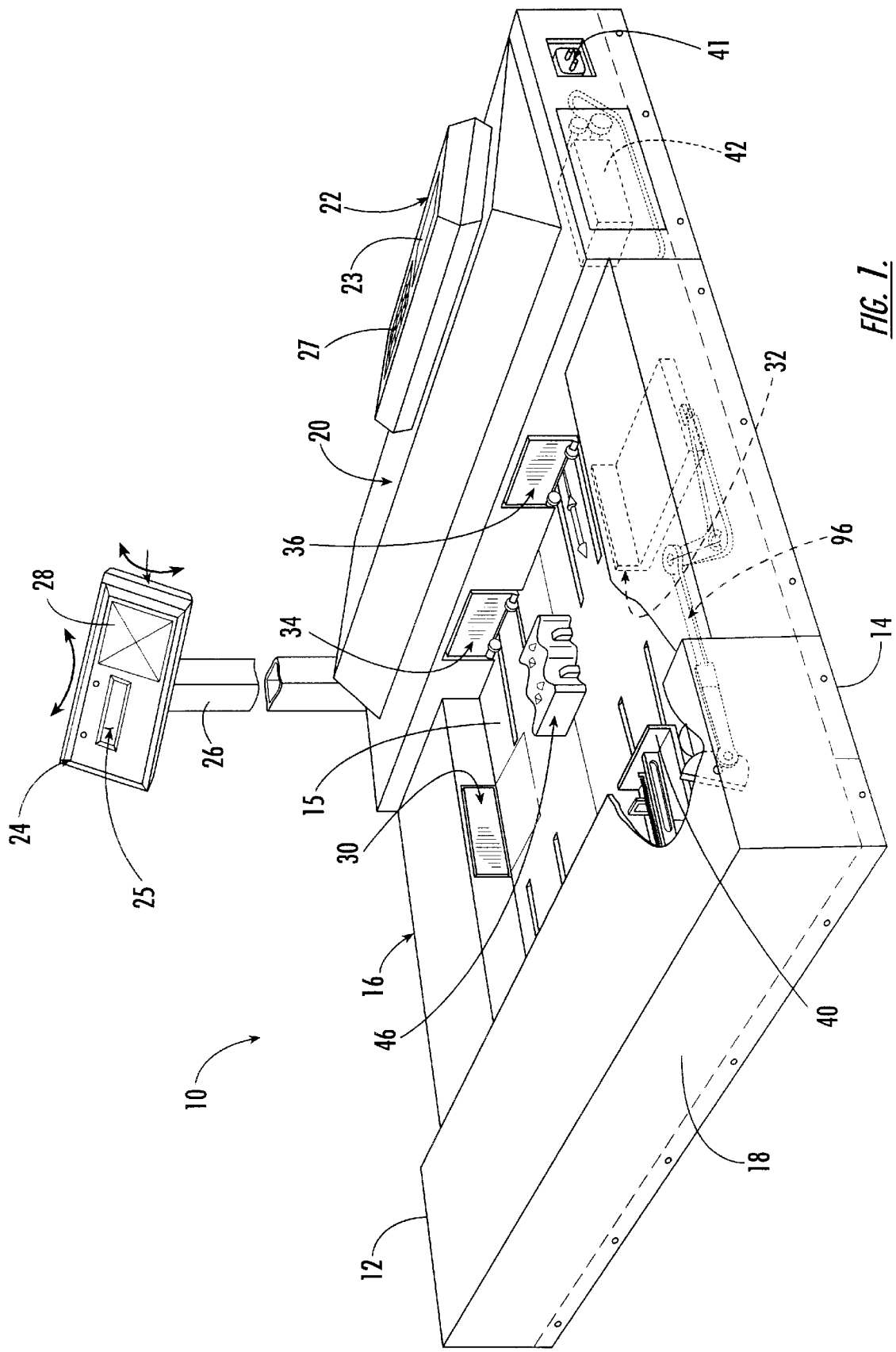
FIG. 1 is a perspective view of an automatic foot-measuring device for measuring two feet simultaneously according to one embodiment of the present invention.
Figure 2:
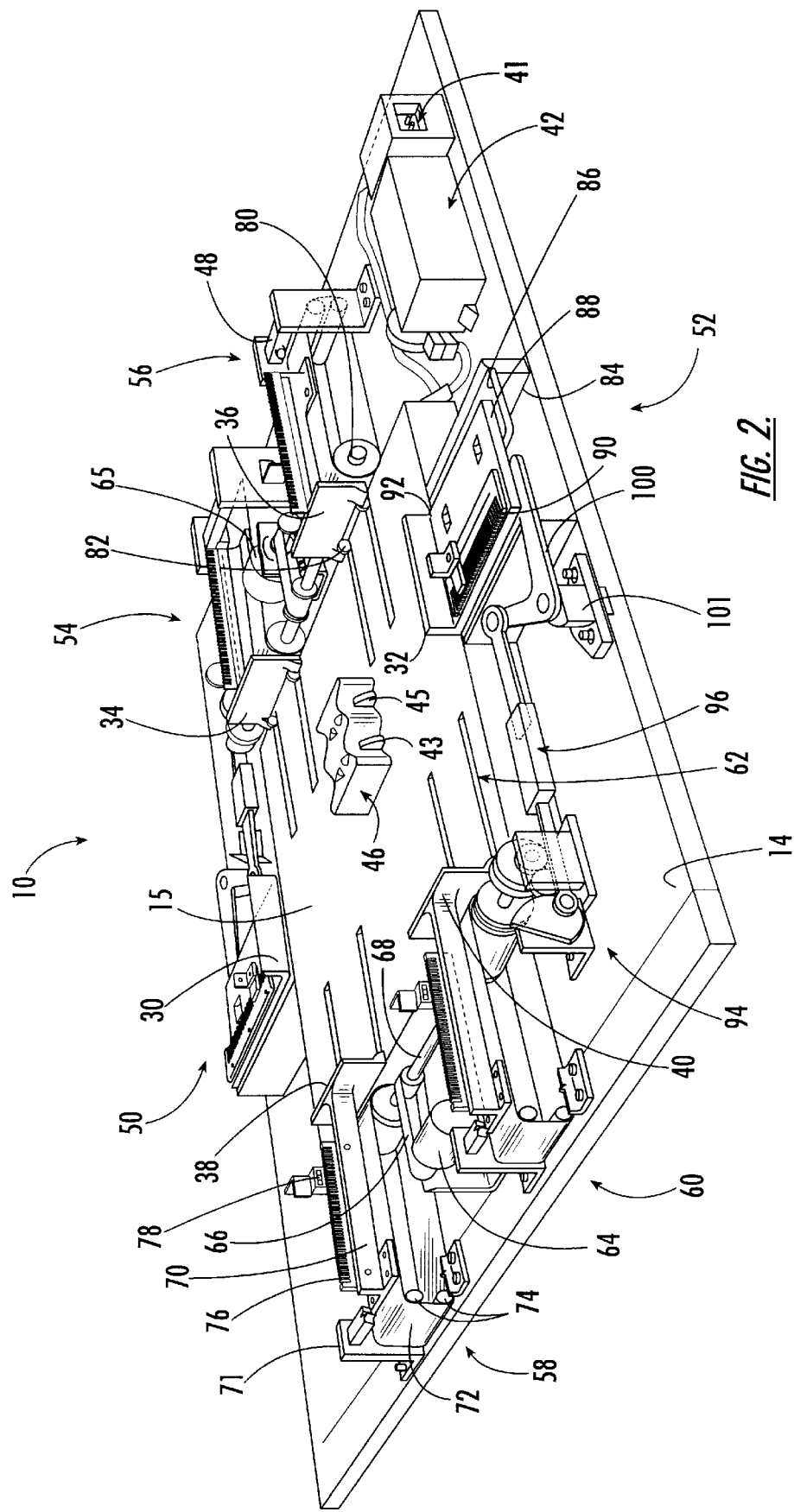
FIG. 2 is a perspective view of the device illustrated in FIG. 1 with the covers removed.

Turning now to the drawings and more particularly to FIGS. 1 and 2, a device for automatically measuring feet to determine shoe size is illustrated generally at 10. FIG. 1 illustrates an embodiment in which two feet may be measured simultaneously. A second embodiment of the present invention, in which only one foot may be measured or in which two feet may be measured sequentially, is illustrated generally at 11 in FIG. 9 and will be discussed in greater detail later.

Referring back to FIGS. 1 and 2, the two-foot measuring device 10 includes a generally rectangular base 14 upon which all of the components of the system are mounted. A foot platform 15 is either mounted onto the center of the base 14 or is integrally formed as a raised portion of the top surface of the base 14. In either case, a housing 12 surrounds the foot platform 15. The housing 12 is formed from a plurality of rectangular boxes with two boxes 16 covering the width measuring devices and elongate, rectangular boxes 18, 20 covering the heel and toe measuring devices, respectively, to define a housing perimeter around the foot platform 15. Although not shown, it should be understood that housing 12 could be stream-lined to provide a less-boxy and more aesthetically-pleasing appearance.

Two control devices are illustrated in FIG. 1. The present invention may be configured for operation with either or both of these control devices. The first control device is illustrated generally at 22 and includes a display 23 and a keypad 27 thereon. The first control device 22 is mounted to the front cover 20 of the device 10. The second control device 24 is mounted at the top of post 26 projecting upwardly from the front cover 20 to place the second control device 24 at a position more easily accessible by the user, whether the customer or device operator. The second control device 24 includes a display 25 and a keypad 28. These control devices 22, 24 include a preprogrammed microprocessor (not shown), which operates the device, converts the mechanical measurements into shoe size recommendations, and has the capability of communicating electronically with an external microprocessor/computer for information transfer.

A recessed male receptacle 41 is built into cover 20, which allows access to a standard 15 volt DC output AC-DC transformer, which can be plugged into a standard AC outlet for supplying electrical power to the device 10. A battery 42 may also be used to supply power to the device 10, as either the primary or back-up power supply.

The housing 12 and the foot platform 15 define a foot well for placement of feet to be measured. The side covers 16, the rear cover 18, and the front cover 20 include openings from which six measuring panels 30, 32, 34, 36, 38, 40 may project into the foot well area for measuring two feet. A ball locator 46 for properly positioning a person's feet on the device 10 is disposed approximately in the center of the foot platform 15. The specific functional operation of the ball locator 46 will be discussed in greater detail later.

As more easily shown in FIG. 2 (with the housing 12 removed), the six measuring panels include two width panels 30, 32, two toe panels 34, 36, and two heel panels 38, 40. Each of the panels is slottedly mounted to the device 10 for sliding movement in and out of a measuring relationship with feet disposed on the foot platform 15. The heel panels 38, 40 are controlled by panel control mechanisms 58, 60, respectively, each of which is driven by a common stepper motor 64 disposed between the two control mechanisms 58, 60. On the opposite side of the base 14, the toe panels 34, 36 are controlled by panel control mechanisms 54, 56, respectively, each of which is driven by a common stepper motor 65 disposed between the two control mechanisms 54, 56. In the embodiment shown in FIG. 2, stepper motor 64 is configured to drive the right width panel 32 using panel control mechanisms 52, and stepper motor 65 is configured to drive the left width panel 30 using panel control mechanism 50; however, it would be easy to reconfigure the device 10 so that each width panel 30, 32 was control by the other stepper motor 64, 65, or by their own stepper motors.

With reference to FIGS. 2–8 generally, the manner in which stepper motors 64, 65 control measurement panels 30, 32, 34, 36, 38, 40 through panel control mechanisms 50, 52, 54, 56, 58, 60 is described in more detail as follows. Toe panels 34, 36 and heel panels 38, 40 are each attached to an elongate support bracket 70 which projects outwardly therefrom to form T-shaped structures. Small wheels 82 are mounted to the lower edge of each panel 34, 36, 38, 40 for movement within parallel grooves 62 to help guide the panels during movement. Each support bracket 70 is mounted to the top surface of an endless belt 72 for reciprocal movement from an "at rest" position (as shown in FIG. 2) to a foot-engagement position (not shown). Each endless belt 72 is trained around a primary drive drum 80 and held in tension around a pair of rollers 74, which are adjustably mounted onto bracket member 71. Endless belt 72 and primary drive drum 80 are mechanically limited to prevent support bracket 70 from over-extending beyond the top surface of the endless belt 72 during extension of the toe and heel panels. When the toe and heel panels are returning to their "at rest" positions, stopper mechanism 48 limits the return distance and helps support bracket 70 return to a consistent "at-rest" position along the top surface of support belt 72.

Figure 3:
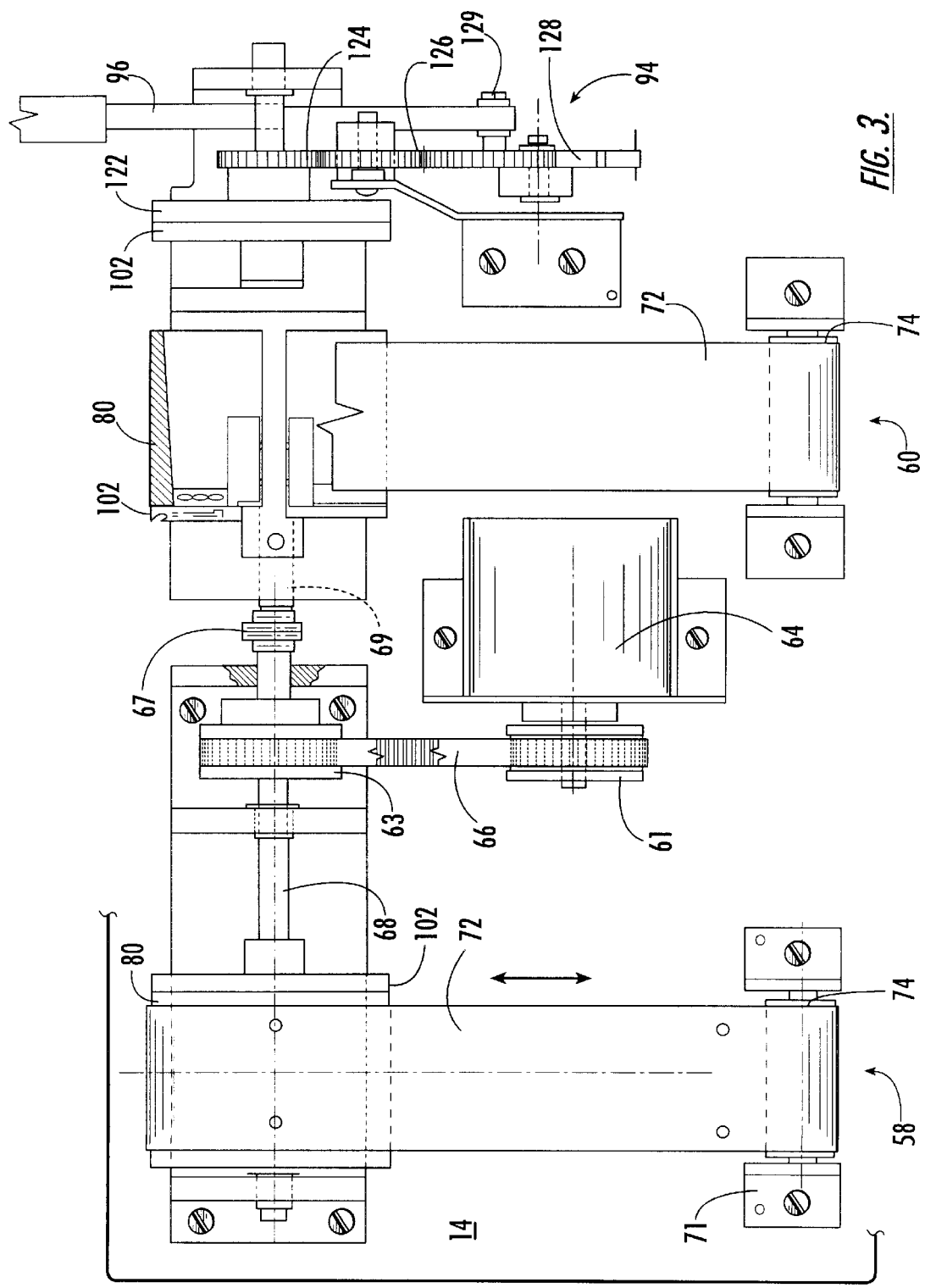
FIG. 3 is a top plan view of the mechanism driving heel measurement devices.
Figure 4:
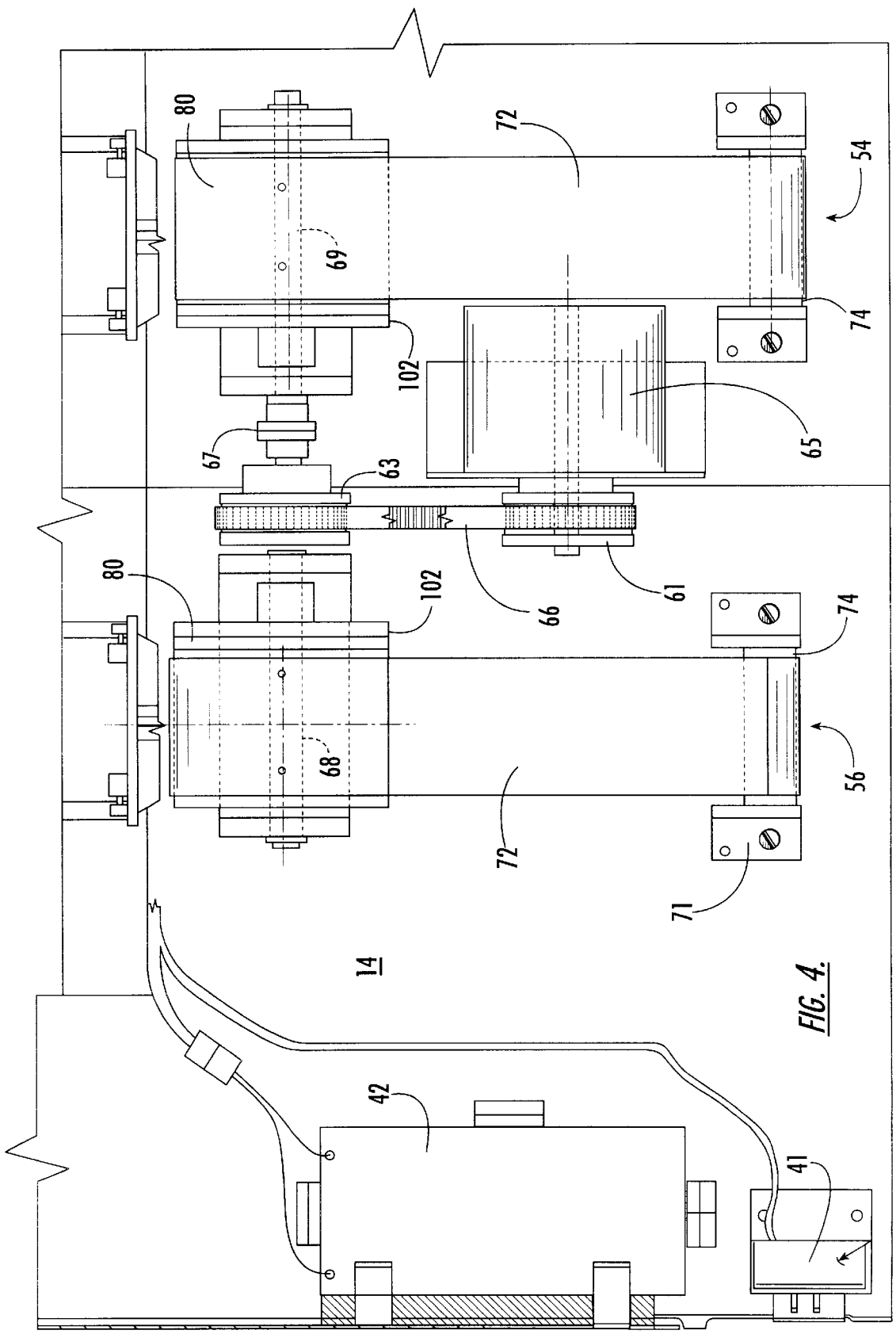
FIG. 4 is a top plan view of the mechanism driving toe measuring devices.

As shown more clearly in FIG. 3 (heel panel control mechanisms) and FIG. 4 (toe panel control mechanisms), each of the stepper motors 64, 65 are operatively attached to drive shaft 68 using a toothed belt 66 which connects pulley members 61, 63. Drive shaft 68 is coupled to a drive shaft extension 69 through a coupling 67. The primary drive drums 80 for panel control mechanisms 54, 56, 58, 60 are mounted on drive shafts 68 and drive shaft extensions 69 and are driven by slip clutches 102. In the preferred embodiment, these slip clutches are either magnetic or electromagnetic, as will be discussed in greater detail later.

Referring to FIGS. 2, 3, 5 and 6, it can be seen that width panels 30, 32 are driven by drive shaft extensions 69 though a gear and link system illustrated generally at 94. More specifically, a magnetic slip clutch 102 mounted on drive shaft extension 69 engages a magnetic plate 122 of an input gear 124. Input gear 124 drives an idler gear 126, which, in turn, drives a larger partial gear 128. One end of mechanical link 96 connects to the larger partial gear 128 through an eccentrically-placed pin 129, while the other end of mechanical link 96 connects at pivot point 99 to one end of bell crank 100. Bell crank 100 is supported at its pivot point 103 at the level of the foot platform 15 by a bracket 101.

Figure 7:
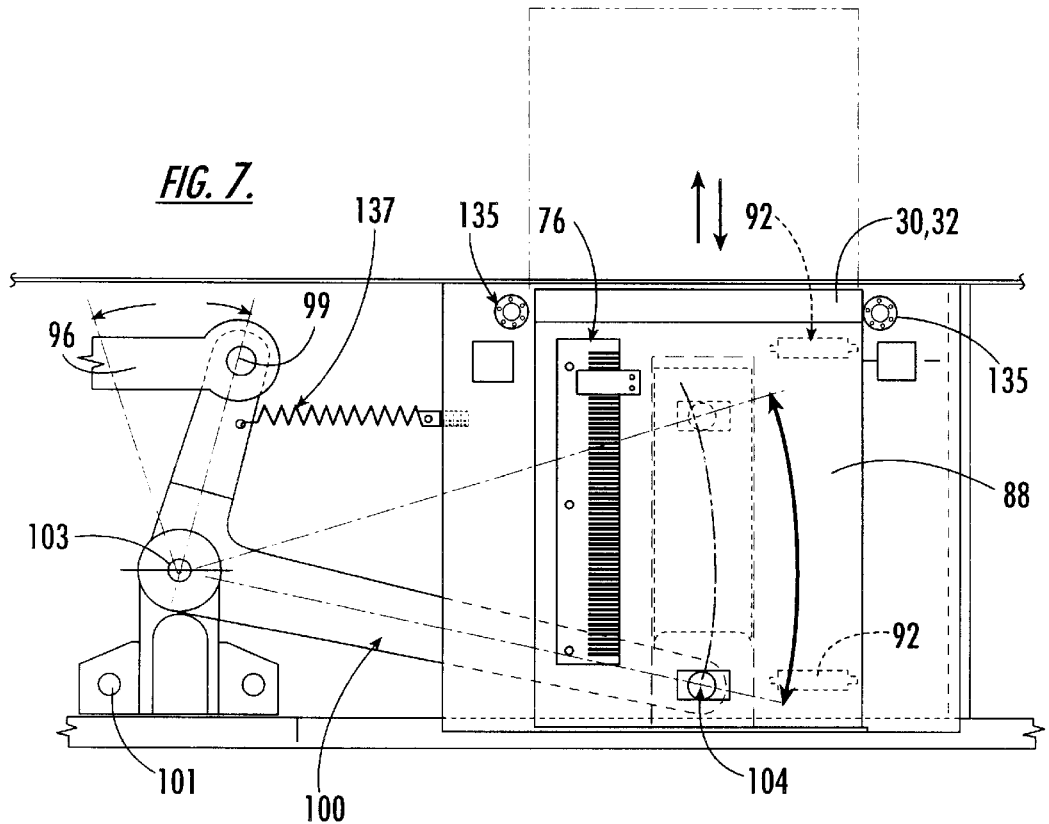
FIG. 7 is a top view of another portion of the mechanism driving width measuring devices.
Figure 8:
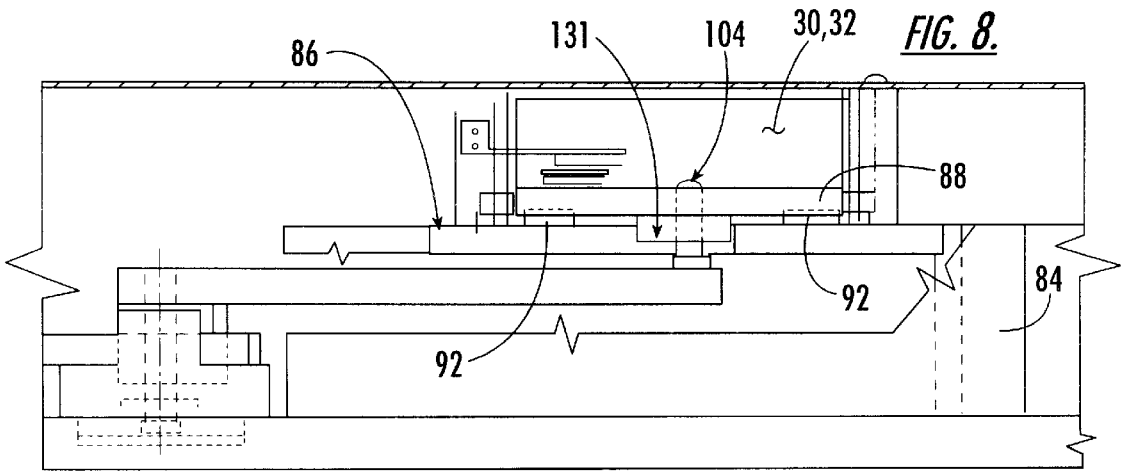
FIG. 8 is a side view of the mechanism illustrated in FIG. 7.

As illustrated in FIGS. 2, 7, and 8, the width panels 30, 32 are mounted to one end of horizontal sliders 88. Horizontal sliders 88 are slidably mounted onto a platform 86 which is supported by two vertically-oriented support members 84. This raises the horizontal slider 88 into a flush position with the foot platform 15. Horizontal sliders 88 roll along platform 86 using rollers 92. A guide block 131 runs along the length of the bottom side of horizontal slider 88 and slidably fits within a slot formed in platform 86. Horizontal slider 88 and width panels 30, 32 extend into engagement with a foot in response to movement of bell crank 100, which connects to horizontal slider 88 and guide block 131 through pin 104. Two ball bearings 135 are assembled on the frame to assist the guide block 131 in maintaining width panels 30, 32 in proper alignment. A spring 137 provides tension to bell crank 100 to assist with panels 30, 32 in returning to their "at rest" positions. In the same manner previously described for the heel and toe panels, magnetic slip clutch 102 allows width panels 30, 32 to extend until coming into contact with a person's foot, even though stepper motors 64, 65 may still be operating and one of the other measuring panels may still be extending.

Figure 9:
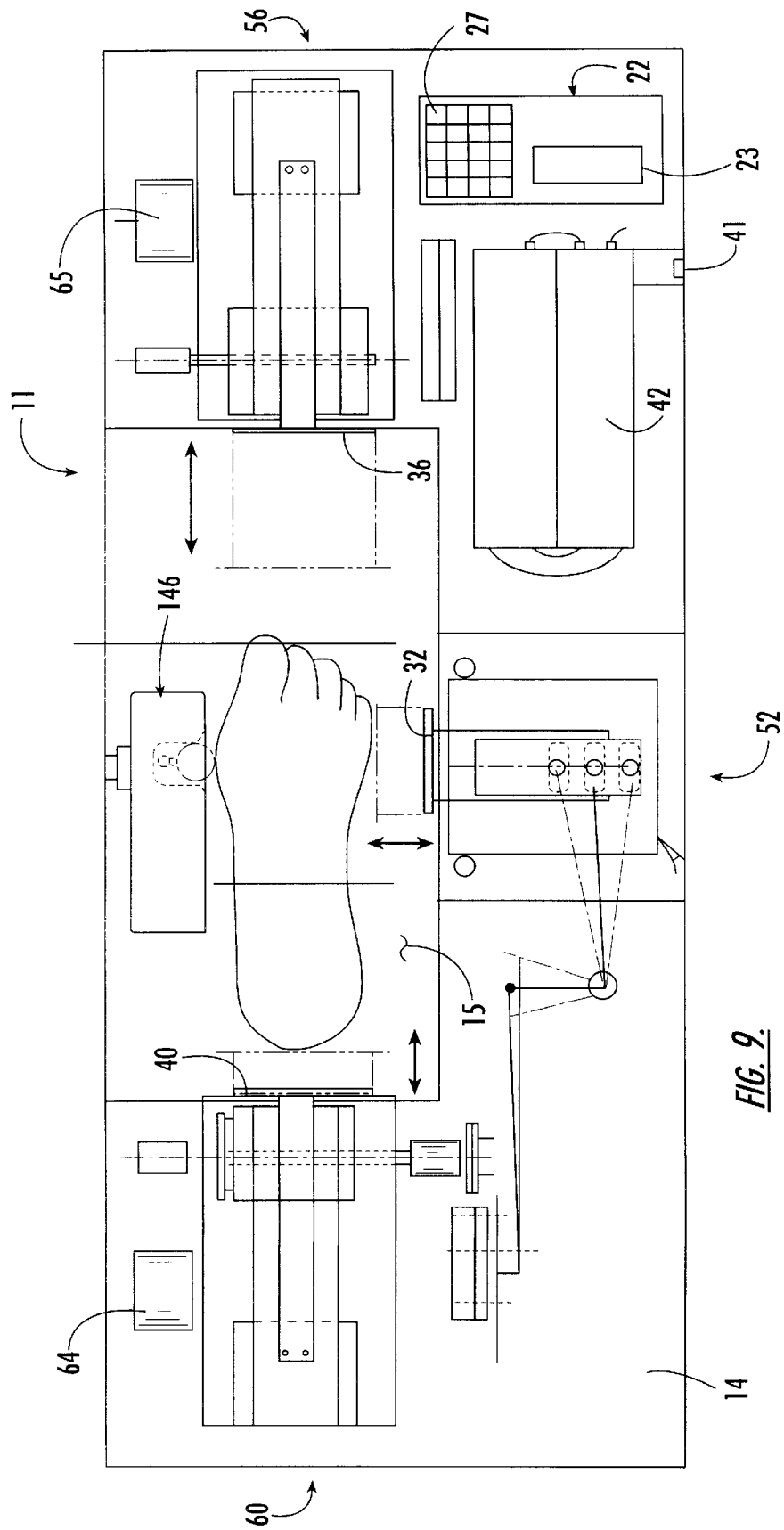
FIG. 9 is a top diagrammatic view of an automatic foot-measuring device for measuring one foot or two feet sequentially according to another embodiment of the present invention.

FIG. 9 illustrates a top view of the one-foot embodiment of the present invention, which is shown generally at 11. Functionally, the one-foot device 11 is essentially the same as the two-foot device 10, with only half of the measuring panels necessary. In other words, device 11 has a base 14, a foot platform 15, a housing 12 (not shown), a control device 22, a display 23, a keypad 27, a preprogrammed microprocessor (not shown), an AC power receptacle 41, and a battery 42. The device 11 also has two stepper motors 64, 65, toe and heel panels 36, 40, and a width panel 32. Width, toe, and heel panel control mechanisms 52, 56, 60, respectively, function in essentially the same manner as previously described for device 10, with one difference being that one drive shaft 68 is sufficient to replace drive shaft 68 and drive shaft extension 69, as shown for device 10. FIG. 9 also illustrates a second embodiment 146 for the ball locator, which will be discussed in greater detail hereinafter. For obvious reasons since only one foot is being measured, the ball locator 146 is located to one side of base 14, opposite the width measuring panel 32, rather than in the center of base 14.

Finally, it should be understood that the one-foot measuring device 11 is mechanically capable of measuring a left foot or a right foot depending solely upon which direction the user is facing. In operation, the user would input which foot was being measured into the microprocessor. Thus, the one-foot device 11 is capable of measuring either one foot or two feet in sequence.

The various embodiments of the ball locators 46, 146, the magnetic and electromagnetic slip clutches 102, and the various embodiments for the measurement system, all of which may be used with either the two foot device 10 or one-foot device 11 will now be discussed in greater detail.

Figure 10:
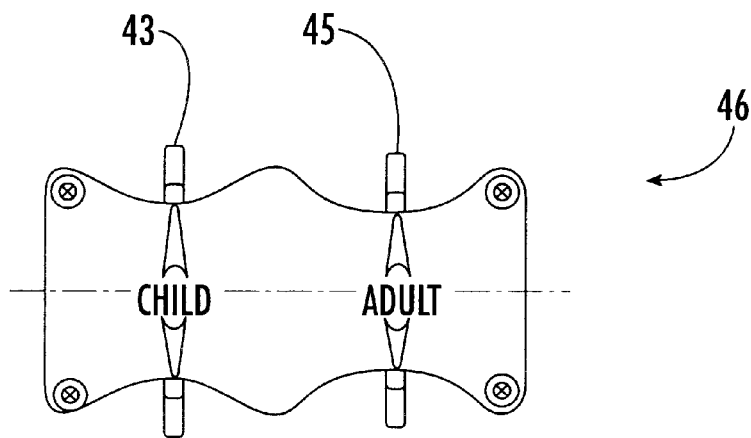
FIG. 10 is a top view of one embodiment of the ball locating system.
Figure 11:
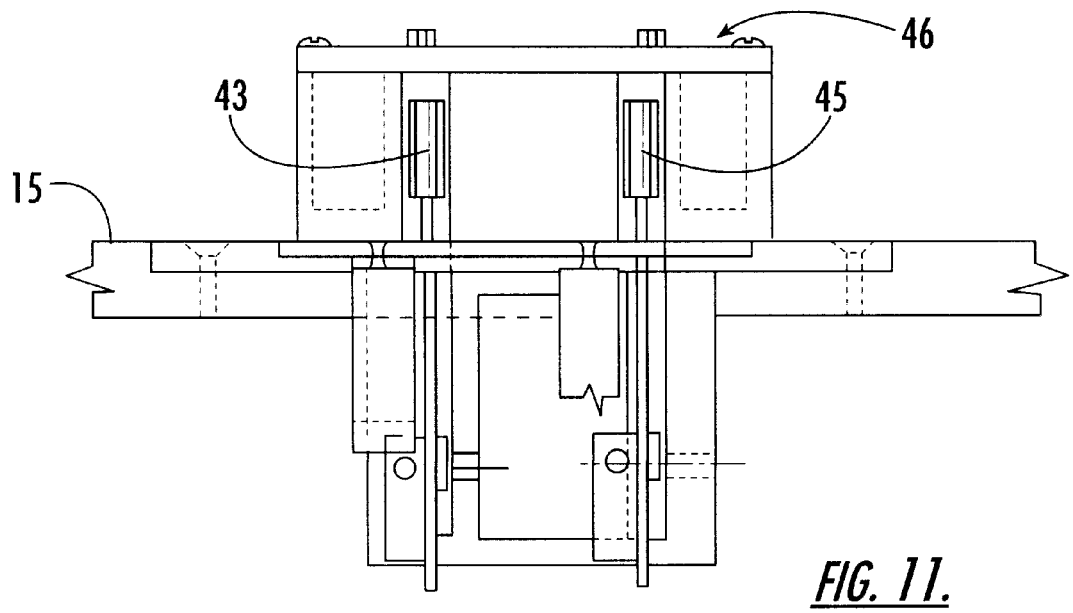
FIG. 11 is a side view of the ball locating system illustrated in FIG. 10.
Figure 12:
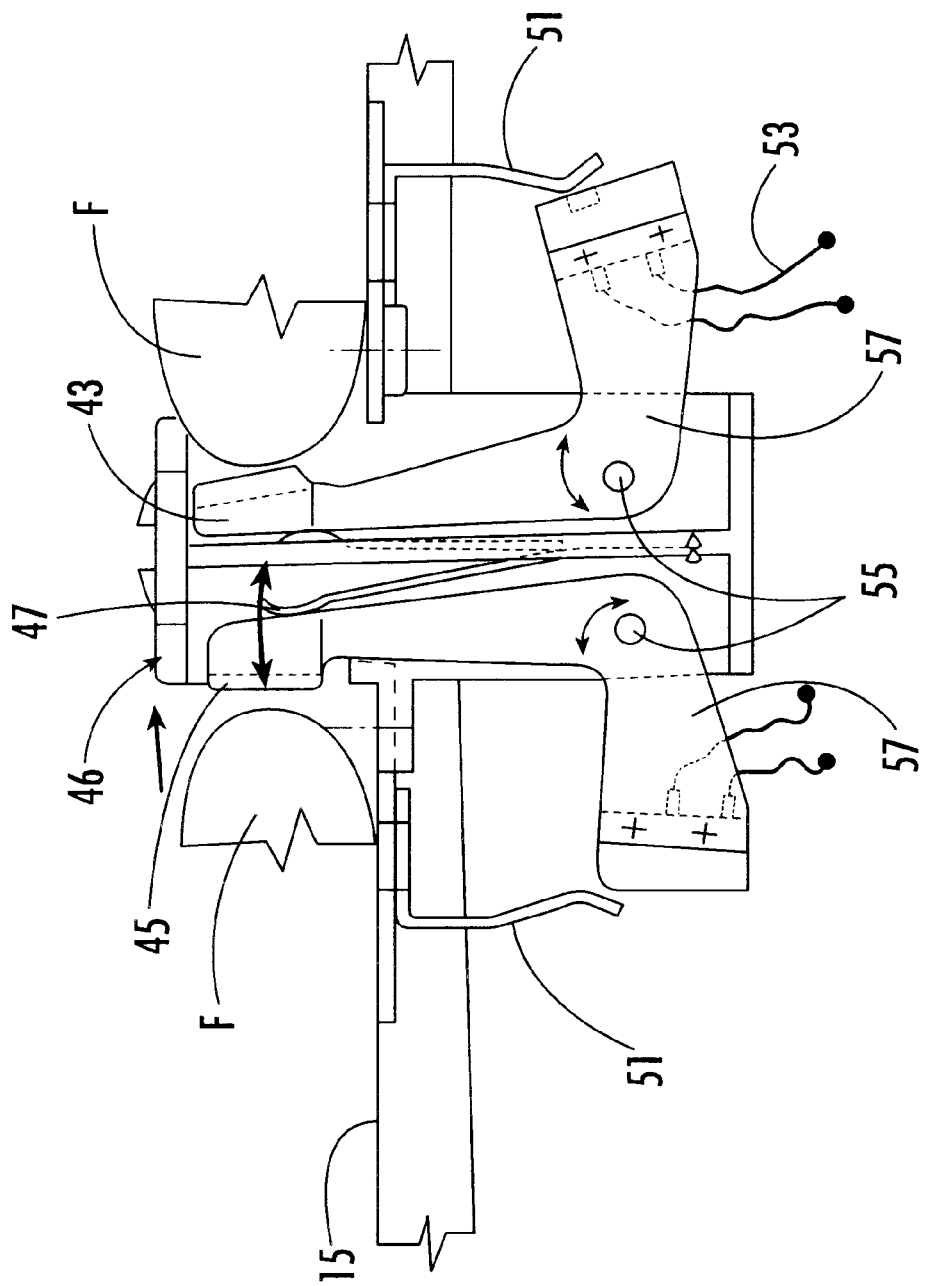
FIG. 12 is another side view of the ball locating system illustrated in FIGS. 10 and 11.

Referring now to FIGS. 10, 11, and 12, one embodiment of the ball locator 46, used with the two-foot measuring device of FIGS. 1 and 2, is illustrated. The ball locator 46 is formed as a generally rectangular block having four concave formations in the side walls thereof. Disposed within each of the four concave formations is a switch, which is activated by the ball of the person's foot when placed in the concave formation. As seen in FIG. 10, two concave formations are defined for a child and two are defined for an adult; thus, accommodating two feet in a parallel relationship. A child-designated switch activator 43 is disposed in two opposing concave formations while an adult-designated switch activator 45 is disposed in the other two concave formations. As seen in FIG. 11, these switch actuators 43, 45 extend below the level of the foot platform 15 for activation when contacted by a person's feet. As seen in FIG. 12, the switch actuators 43, 45 include generally L-shaped arms 57 which are mounted to the ball locator 46 at pivot points 55. Contact with the ball of a person's foot F causes the L-shaped arm 57 to pivot into electric contact with arms 51, which completes a circuit using wiring 53 for the dual purpose of activating the measuring device and for indicating whether the person being measured is an adult or a child. Springs 47 ensure that switch activators 43 and 45 return to an extended and ready position when not depressed by the ball of a foot F. FIG. 12 shows switch activator 43 depressed and switch activator 45 in an extended and ready position.

In another embodiment (not shown) of the two-foot measuring device, the ball locator 46 may be formed as a generally rectangular block having two concave formations in the side walls thereof with one on either side of the block. Electrically and mechanically, the switch activators 43, 45 would be identical to the description previously given. Rather than having a different switch activator for an adult and a child, however, a single switch activator would be used and the customer or device operator would merely input into the device microprocessor whether the customer being measured was an adult or a child.

FIGS. 13 and 14 illustrate another embodiment of the ball locator designated generally at 146. In this embodiment, used with a one-foot measuring device 11 as shown in FIG. 9, the ball locator 146 is formed as a generally rectangular block or housing 144 having only one concave formation in one of the side walls thereof. It should be understood that this one concave formation can be used for adults or children, with the customer or operator being able to input into the device microprocessor whether the customer being measured was an adult or a child. Disposed within the concave formation is a switch activator 145, which is activated by the ball of the person's foot when placed in the concave formation. In this embodiment, the switch actuator 145 does not extend below the level of the foot platform 15, but is contained with the housing 144, which mounts to the foot platform 15. The switch actuator 145 includes a head 148 and a shaft 150, which is slidably mounted within a channel 168 within the housing 144. The housing 144 also has two chambers 164, 166. A switch rod 152 is mounted within chamber 164 at pivot point 155 and connects at one end to the shaft 150 of the switch activator 145. Mounted on the other end of the switch rod 152 is a magnet 157, which is disposed a fixed distance from a Hall Effect sensor 160. Flat spring 162 ensures that switch actuator 145 remains in an extended position within the concave formation when not depressed by the ball of a foot.

In operation, when the ball of a person's foot contacts the switch activator 145, the head 148 and shaft 150 are depressed and slide into the housing 144 along channel 168. The switch rod 152 pivots about pivot point 155 so that magnet 157 is brought into proximity to Hall Effect sensor 160. The Hall Effect sensor 160 can be advantageously used for several purposes. First, it can merely act as an on/off switch to detect when a person's foot has been properly placed against the ball locator within the foot well of the device 10 or 11. Second, since the Hall Effect sensor 160 generates an increasingly stronger electrical signal as the magnet 157 draws closer, this signal can be used to determine the relative size of the ball of the foot of the person being measured. The more the switch activator 145 is depressed, the greater the signal generated by the Hall Effect sensor 160, and the larger the ball of the foot of the person being measured. Conversely, the less the switch activator 145 is depressed, the weaker the signal generated by the Hall Effect sensor 160, and the smaller the ball of the foot of the person being measured.

Although only three embodiments for the ball locator are discussed in detail above, it should be generally understood that any one or any combination of these designs can be used with the one-foot or two-foot embodiments of the present invention. Thus, the number of switch activators used in the present invention could range from one to four or more, depending upon whether the device was designed for measuring one or two feet simultaneously and whether the designation of adult, male, female, or child was input into the device microprocessor or indicated by the activation of a particular switch activator.

As previously stated, the slip clutch 102 can be advantageously used to allow the stepper motors 64, 65 to continue driving all of the engagement panels until all of the panels have properly engaged a surface of the person's foot. The slip clutch 102 enables the panels to be driven until coming into contact with the foot but insures that the amount of pressure exerted on the foot is comfortable. A slip clutch 102 of a standard frictional type could be used; however, a magnetic or electromagnetic slip clutch should provide for a longer life of the clutch and minimize the amount of maintenance and adjustments necessary.

Figure 15:
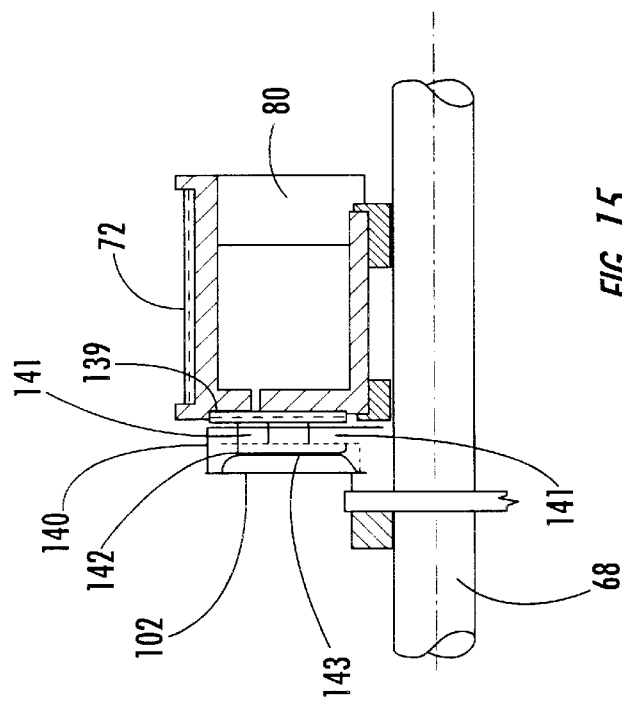
FIG. 15 is a side cross-sectional view of one embodiment of a slip clutch.

FIG. 15 presents a side cross-sectional view of a slip clutch 102 using magnetism to engage a primary drive drum 80. Slip clutch 102 has a nonmetallic platen 140, which is fixedly attached to drive shaft 68. Platen 140 has several apertures in which permanent earth magnets 141 may be placed or "floated." Magnets 141 are retained from within the slip clutch 102 using a metallic plate 142, which is forced into contact with the magnets 141 using a non-metallic retaining spring 143. A metallic clutching plate 139, which is fixedly mounted and bonded onto one end of primary drive drum 80, contacts the other side of magnets 141 since the width of the magnets 141 is slightly greater than the width of the apertures in platen 140. Further, the polarity of the magnets 141 are oppositely aligned so that a magnetic circuit/coupling is created between plates 139, 142 through magnets 141. Thus, when drive shaft 68 rotates, platen 140 rotates, which causes the magnets 141 to rotate. The magnetic coupling through magnets 141 exerts a torque on plate 139, which causes drum 80 to rotate. In the preferred embodiment, three sets of magnet pairs may be distributed around the slip clutch (at 120° intervals) to evenly distribute the magnetic torque applied to the drum 80. The magnetic strength of the magnets 141 is chosen to be generally sufficient to rotate the drum 80 but causing the clutch to slip once the engagement panel which drum 80 is driving engages the surface of a person's foot, giving a comfortable pressure against the foot.

Figure 16:
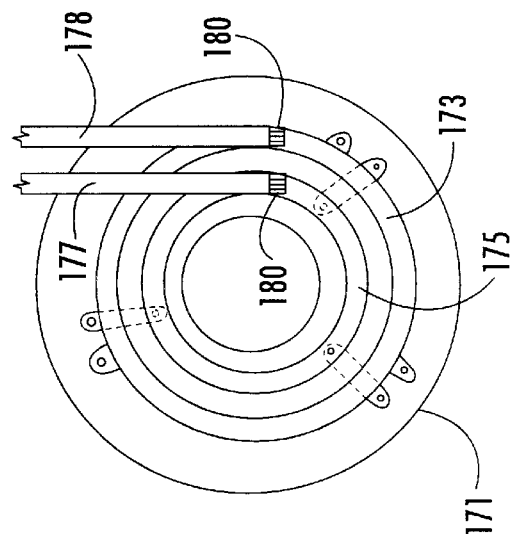
FIG. 16 is a side view of a PC board used in another embodiment of a slip clutch.

An electromagnetic slip clutch could be used in a manner similar to that previously described for the permanent magnetic slip clutch. However, an electromagnetic slip clutch has the advantage of being able to vary the magnetism, and thus the torque exerted by the slip clutch 102, by varying the voltage supplied to the electro-magnets. Despite this advantage, such a slip clutch is more difficult and expensive to manufacture. For example, as seen in FIG. 16, in order to supply voltage to a rotating electro-magnet, it is necessary to mount a circular PC board 171 to the slip clutch 102. The PC board 171 has two concentric conductive rings 173, 175, which are connected to the positive and negative terminals of the electromagnets, respectively. Two power supply wires 177, 178 from the device AC-DC transformer or battery 42 provide voltage to the conductive rings 173, 175 through flexible, conductive brushes 180. Such brushes 180 provide sufficient electrical contact between the power supply wires 177, 178 and the conductive rings 173, 175, regardless of which direction the drive shaft 68 and slip clutch 102 rotate.

Referring back to FIGS. 2, 5, and 7, the measurement system of the present invention will now be described in greater detail. As previously stated, the present invention measures the size of a person's foot indirectly by measuring how far each panel moves from its "at rest" position until contacting the foot. More specifically, the preprogrammed microprocessor, having been preprogrammed with the specific distances between the toe panels 34, 36 and heel panels 38, 40, respectively, in their "at rest" positions and between the ball locator 46 or 146 and the width panels 30, 32 in their "at rest" positions, can calculate the person's shoe size.

In one embodiment, a comb-like structure track 76 is mounted to the support bracket 70 of the heel and toe panels 34, 36, 38, 40 and is mounted to the slider 88 associated with each width panel 30, 32. A light-emitting diode (LED) 78 is provide along with a photocell sensor adjacent the comb 76 and in alignment therewith such that as the comb 76 is caused to move linearly (when the panels are being extended), the photocell senses a series of openings and blocking members. By counting the spaces, a fairly accurate determination (down to one-sixth of a universal shoe size interval) may be made as to the distance that the panel had to extend to contact the person's foot.

In another embodiment, illustrated in FIGS. 19 and 20, an LED 78 can be mounted across from a photosensitive transistor 79. A photo-etched glass plate 73 having a series of evenly spaced slots is mounted to the support bracket 70 or slider 88 and disposed between the LED 78 and photosensitive transistor 79. As the panels and, thus, the glass plate 73 move, the transistor 79 counts the number of light pulses passing through the slots in the glass plate 73. This embodiment also provides a fairly accurate determination (down to one-fourth of a shoe size interval) of the distance the panel had to extend to contact the person's foot. For even more accurate measurements (down to one-eighth of a shoe size interval), two sets of LEDs 78 and photosensitive transistors 79 can be positioned across from each. In this embodiment, the photoetched glass plate can be manufactured to have two offset rows of alternating slots other (as illustrated in FIGS. 19 and 20). One row of slots is disposed between one LED/transistor pair and the other row is disposed between the other LED/transistor pair. As can be seen in FIG. 20, the slots and rows are offset so that, as the panel and glass plate move, light from the diodes will alternate passing through one slot in one row at a time. This embodiment basically doubles the accuracy available with only one LED/transistor pair and one row of slots.

Figure 17:
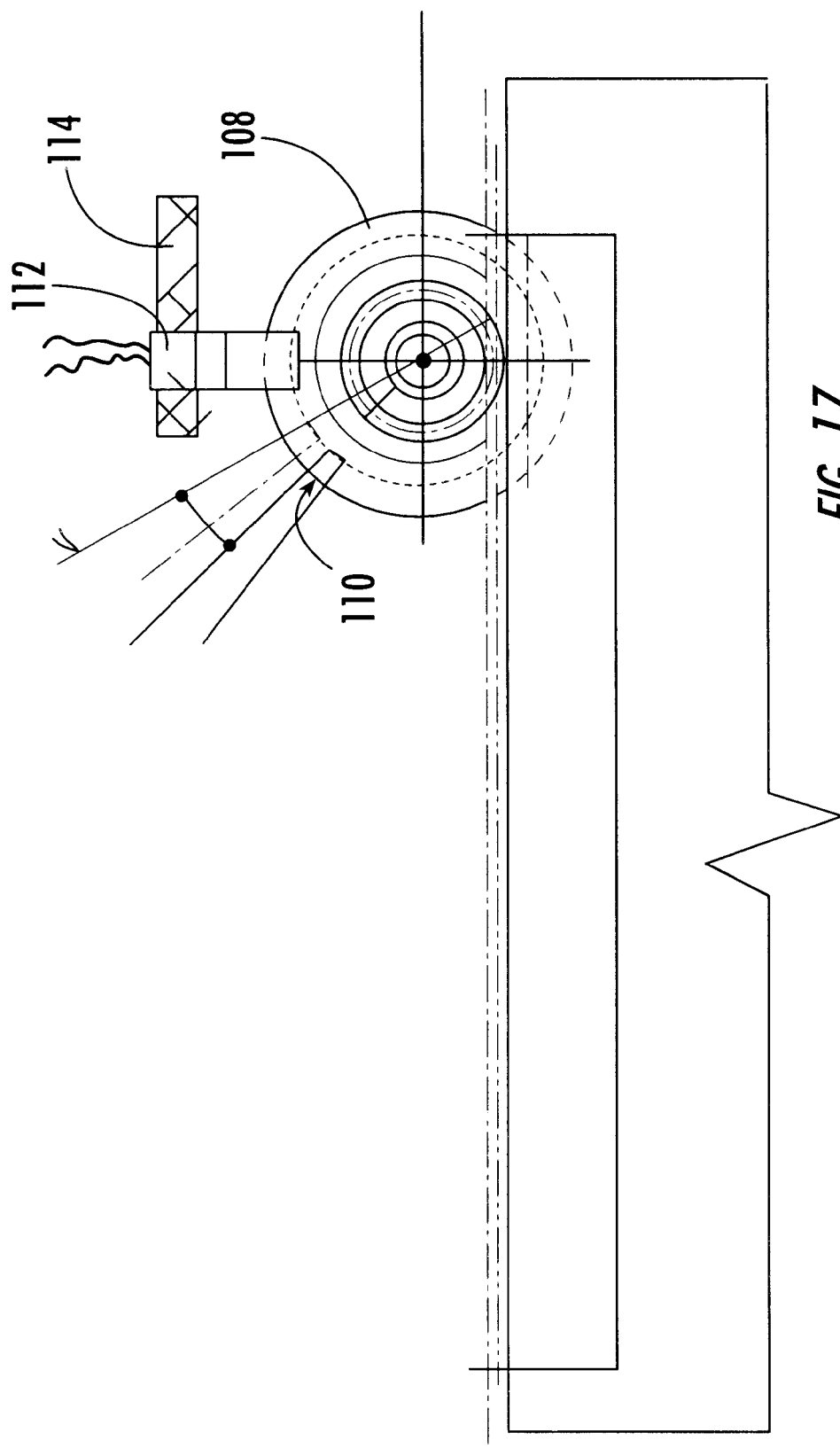
FIG. 17 is a side diagrammatic view of one embodiment for measuring the distance traveled by measurement panels.
Figure 18:
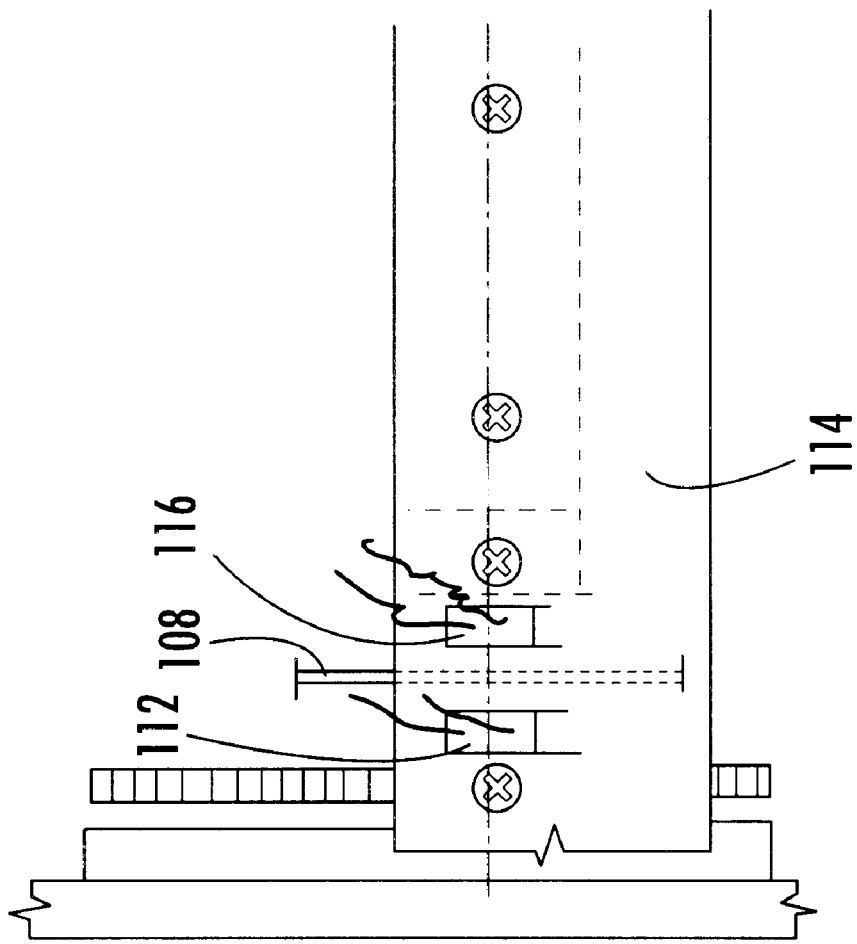
FIG. 18 is a top plan diagrammatic view of the measurement system illustrated in FIG. 17.

With reference to FIGS. 17 and 18, it should also be noted that, instead of using a linear comb or plate as described in either of the above two embodiments, a circular disk having notches or slots formed therein could alternatively be used to determine the distance each panel travels. For example, a rotary notched "gear" 108 is mounted to the device for rotational driving movement by slider mechanisms. Each wheel 108 includes a plurality of notches 110 formed therein at predetermined intervals. An LED sensor 112 is mounted to a bracket 114 at a position wherein the sensor may interact with the notches. As seen in FIG. 18, an LED 116 is mounted opposite the receiver 112 such that each movement of a notch by the LED counts as one increment which is recorded by the microprocessor.

In operation of the preferred one-foot embodiment, a person presses the start button on the keypad 28 of the control device 24. The person then inputs whether he is a male or female, adult or child, whether his instep is high or average, and whether he wants to measure his right foot or left foot first. The person then steps onto the platform 15 and places his foot against switch activator 146. Once the Hall Effect sensor 160 maintains a relatively fixed electrical signal, which indicates that the foot is properly placed and the ball of the foot is completely inserted, the microprocessor activates the stepper motors 64, 65. Panels 32, 36, 40 extend from their "at rest" positions until all three have engaged a surface of the foot. After a brief predetermined period of engagement by all three panels 32, 36, 40, the microprocessor reverses the stepper motors until the panels have returned to their "at rest" positions. The photosensitive transistors 79 for each panel transmit the distance each panel has traveled before engaging the person's foot and the Hall Effect sensor 160 indicates the size of the ball of the person's foot. The preprogrammed microprocessor then converts this raw measurement data into a standard shoe size in United States units. This shoe size is displayed, along with alternative shoe size recommendations, on display 25 for a predetermined period of time, such as, for example, 15 to 45 seconds. If the person wants to convert this information into shoe size units of a different country or for a particular shoe manufacturer, such a request can be input into keypad 28. The person can then repeat the above process to measure his other foot, if desired. All of this shoe size data is recorded in computer memory associated with the microprocessor for later retrieval or download by the person, shoe retailer, or shoe manufacturer.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A powered device for automatically measuring at least one foot to determine shoe size comprising:
   a base for placement thereon of the foot being measured;
   a switch means mounted on said base in a disposition to be proximate the ball of the foot when placed on said base, said switch means being activated by proximity of the ball of the foot;

a motor means mounted on said base, said motor means comprising a first and second stepper motor;

at least three panels movably mounted on said base, said at least three panels including a heel engagement panel for engaging the heel, a toe engagement panel for engaging the toe projecting forwardmost from the foot, and an edge engagement panel for engaging the outer edge of the foot, said heel engagement panel and said edge engagement panel being driven by said first stepper motor and said toe engagement panel being driven by said second stepper motor;

distance determining means associated with each of said panels for producing data representing the distance each of said panels travels from a known starting position until engaging the heel, the forwardmost toe, and the outer edge of the foot;

a microprocessor in communication with said switch means, said motor means, and said distance determining means for detecting activation of said switch means by the ball of the foot, for controlling said motor means, for receiving the distance-representing data from said distance determining means, and for converting said distance-representing data into a shoe size; and wherein said heel engagement panel and said toe engagement panel are each moved by a first panel control mechanism and said edge engagement panel is moved by a second panel control mechanism, said first panel control mechanism comprising:
 a first roller rotatably mounted a predetermined distance above the surface of said base;
 a second roller mounted to a drive shaft rotatably driven by said first stepper motor;
 an endless belt disposed around said first and second rollers for movement in response to rotation of said second roller; and
 a support bracket mounted on one end thereof to said endless belt and connected at the other end thereof to one of said heel and toe engagement panels for extension thereof in response to movement of said endless belt from said known starting position until engaging the foot; and said second panel control mechanism comprising:
 at least one gear mounted to said drive shaft rotatably driven by said first stepper motor;
 a support structure mounted on said base proximate the outer edge of the foot;
 a slider moveably mounted to said support structure, said edge engagement panel fixedly connected to one end of said slider; and
 a mechanical link system mounted at one end thereof to said slider and eccentrically mounted at the other end thereof to said at least one gear, said mechanical link system converting the rotating movement of said at least one gear into a linear movement of said slider whereby said edge engagement panel is extended from said known starting position until engaging the outer edge of the foot in response to rotation of said at least one gear.

2. The device according to claim 1 further comprising a slip clutch for engaging said drive shaft with said second roller and said at least one gear.

3. The device according to claim 2 wherein said slip clutch is a magnetic slip clutch, an electromagnetic slip clutch, or a friction slip clutch.

4. The device according to claim 1 wherein said distance determining means associated with each of said panels comprises:

an elongate comb having a plurality of evenly-spaced light-reflecting members with openings therebetween, said elongate comb fixedly mounted to one of said support bracket and said slider;

an LED mounted to one side of said elongate comb for directing light toward the plurality of light-reflecting members and openings of said elongate comb; and a photocell sensor mounted adjacent said LED for detecting light reflected from said elongate comb whereby the distance each of said panels moves from said known starting position until engaging the foot can be determined by counting the number of reflections from said elongate comb as said elongate comb moves along with said support bracket or said slider.

5. The device according to claim 1 wherein said distance determining means associated with each of said panels comprises:

a rotary comb having a plurality of evenly-spaced light-reflecting members with openings therebetween, said rotary comb rotatingly mounted adjacent one of said support bracket and said slider for rotating in response to movement thereof;

an LED mounted to one side of said comb for directing light toward the plurality of light-reflecting members and openings of said rotary comb; and a photocell sensor mounted adjacent said LED for detecting light reflected from said rotary comb whereby the distance each of said panels moves from said known starting position until engaging the foot can be determined by counting the number of reflections from said rotary comb as said rotary comb rotates in response to movement of said support bracket or said slider.

6. The device according to claim 1 wherein said distance determining means associated with each of said panels comprises:

an elongate plate having a first row of a plurality of evenly-spaced slots, said elongate plate fixedly mounted to said support bracket or said slider;

a first LED mounted to one side of said elongate plate for directing light toward said first row of evenly-spaced slots; and a first photocell sensor mounted opposite said first LED on the other side of said elongate plate for detecting light from said first LED passing through said first row of evenly-spaced slots whereby the distance each of said panels moves from said known starting position until engaging the foot can be determined by counting the number of times light passes through a slot in said elongate plate as said elongate plate moves along with said support bracket or said slider.

7. The device according to claim 6 wherein said elongate plate further includes a second row of evenly-spaced slots parallel to and horizontally-offset from said first row of evenly-spaced slots, said distance determining means associated with each of said panels further comprising:

a second LED mounted to one side of said elongate plate for directing light toward said second row of evenly-spaced slots; and a second photocell sensor mounted opposite said second LED on the other side of said elongate plate for detecting light from said second LED passing through slots in said elongate plate whereby the distance each of said panels moves from said known starting position until engaging the foot can be determined by counting the number of times light passes through a slot in alternating rows of said elongate plate as said elongate plate moves along with said support bracket or said slider.

8. The device according to claim 1 wherein said distance determining means associated with each of said panels comprises:
   a rotary plate having a plurality of evenly-spaced slots, said rotary plate rotatingly mounted adjacent one of said support bracket and said slider for rotating in response to movement thereof;
   an LED mounted to one side of said rotary plate for directing light toward the plurality of evenly-spaced slots in said rotary plate; and
   a photocell sensor mounted opposite said LED on the other side of said rotary plate for detecting light from said LED passing through the slots of said rotary plate whereby the distance each of said panels moves from said known starting position until engaging the foot can be determined by counting the number of times light passes through a slot in said rotary plate as said rotary plate rotates in response to movement of said support bracket or said slider.

9. The device according to claim 1 and further comprising:
   a keypad mounted to said base and in communication with said microprocessor for entering data into said microprocessor; and
   a display mounted to said base for displaying data entered with said keypad and for displaying data generated by said microprocessor.

10. The device according to claim 9 wherein said microprocessor displays the distance-representing data in country-specific shoe sizes on said display.

11. The device according to claim 9 wherein said microprocessor displays the distance-representing data in manufacturer-specific shoe sizes on said display.

12. The device according to claim 9 wherein said device can measure a right or a left foot in response to data entered with said keypad.

13. The device according to claim 9 and further comprising memory means in communication with said microprocessor whereby the distance-representing data may be stored for later access or download.

14. A powered device for automatically measuring at least one foot to determine shoe size comprising:
   a base for placement thereon of the foot being measured;
   a switch means mounted on said base in a disposition to be proximate the ball of the foot when placed on said base, said switch means being activated by proximity of the ball of the foot;
   a motor means mounted on said base;
   at least three panels movably mounted on said base, said at least three panels including a heel engagement panel for engaging the heel, a toe engagement panel for engaging the toe projecting forwardmost from the foot, and an edge engagement panel for engaging the outer edge of the foot, movement of said panels being driven by said motor means;
   distance determining means associated with each of said panels for producing data representing the distance each of said panels travels from a known starting position until engaging the heel, the forwardmost toe, and the outer edge of the foot;
   a microprocessor in communication with said switch means, said motor means, and said distance determining means for detecting activation of said switch means by the ball of the foot, for controlling said motor means, for receiving the distance-representing data from said distance determining means, and for converting said distance-representing data into a shoe size; and
   wherein said switch means further comprises:
      a generally rectangular housing mounted on said base and having a concave formation in a side wall thereof adapted for receiving the ball of the foot;
      an electrical contact mounted within said housing;
      a spring mounted within said housing;
      a switch activator pivotally mounted within said housing, said switch activator generally being in open-circuit electrical communication with said microprocessor, one end of said switch activator extending from within said housing into the concave formation in response to tension from said spring for engagement with the ball of the foot, the other end of said switch activator having an electrically-conductive surface, the electrically-conductive surface pivoting into contacting with said electrical contact and causing said switch activator to become in closed-circuit communication with said microprocessor when said switch activator is depressed in response to placement of the ball of the foot within the concave formation.

15. A powered device for automatically measuring at least one foot to determine shoe size comprising:
   a base for placement thereon of the foot being measured;
   a switch means mounted on said base in a disposition to be proximate the ball of the foot when placed on said base, said switch means being activated by proximity of the ball of the foot;
   a motor means mounted on said base;
   at least three panels movably mounted on said base, said at least three panels including a heel engagement panel for engaging the heel, a toe engagement panel for engaging the toe projecting forwardmost from the foot, and an edge engagement panel for engaging the outer edge of the foot, movement of said panels being driven by said motor means;
   distance determining means associated with each of said panels for producing data representing the distance each of said panels travels from a known starting position until engaging the heel, the forwardmost toe, and the outer edge of the foot;
   a microprocessor in communication with said switch means, said motor means, and said distance determining means for detecting activation of said switch means by the ball of the foot, for controlling said motor means, for receiving the distance-representing data from said distance determining means, and for converting said distance-representing data into a shoe size; and
   wherein said switch means further comprises:
      a generally rectangular housing mounted on said base and having a concave formation in a side wall thereof adapted for receiving the ball of the foot;
      a Hall Effect sensor mounted within said housing and in electrical communication with said microprocessor, said Hall Effect sensor generating an electrical signal when in the proximity of a magnetic field;
      a spring mounted within said housing;
      a switch activator moveably mounted within said housing, one end of said switch activator extending from within said housing into the concave formation in response to tension from said spring for engagement with the ball of the foot; and an arm pivotally mounted within said housing, one end of said arm having a magnet mounted thereon, the other end of said arm connected to said switch activator whereby said arm is caused to pivot, the magnet is brought into proximity to said Hall Effect sensor, and said Hall Effect sensor sends an electrical signal to said microprocessor when said switch activator is depressed in response to placement of the ball of the foot within the concave formation.

16. The device according to claim 15 wherein the strength of the electrical signal generated by said Hall Effect sensor varies according to how far said switch activator is depressed in response to placement of the ball of the foot within the concave formation and whereby the relative size of the ball of the foot may be determined by the strength of the electrical signal.

* * * * *